US008743191B2

(12) United States Patent
Davidson et al.

(10) Patent No.: US 8,743,191 B2
(45) Date of Patent: Jun. 3, 2014

(54) SYSTEM AND METHOD FOR EDITING AN IMAGE STREAM CAPTURED IN VIVO

(75) Inventors: Tal Davidson, Yoqneam Illit (IL); Michael Skala, Zichron Yaaqov (IL); Hagai Krupnik, Nofit (IL); Eli Horn, Kiryat Motzkin (IL)

(73) Assignee: Given Imaging Ltd., Yoqneam (IL)

(*) Notice: Subject to any disclaimer, the term of this patent is extended or adjusted under 35 U.S.C. 154(b) by 309 days.

(21) Appl. No.: 13/161,845

(22) Filed: Jun. 16, 2011

(65) Prior Publication Data
US 2011/0243523 A1 Oct. 6, 2011

Related U.S. Application Data

(63) Continuation of application No. 10/949,220, filed on Sep. 27, 2004, now Pat. No. 7,986,337.

(51) Int. Cl.
*H04N 7/18* (2006.01)
*H04N 9/47* (2006.01)

(52) U.S. Cl.
USPC ............. 348/77; 348/65; 348/68; 348/333.05

(58) Field of Classification Search
USPC .................. 348/77, 65, 68, 333.05
See application file for complete search history.

(56) References Cited

U.S. PATENT DOCUMENTS 6,339,446 B1 * 1/2002 Miyoshi .......................... 348/65
7,319,781 B2 * 1/2008 Chen et al. .................... 382/128

FOREIGN PATENT DOCUMENTS

JP 10112835 4/1998
JP 2004521662 7/2004

OTHER PUBLICATIONS

Office Action issued on May 10, 2011 for Japanese Application No. 2005-279235.

* cited by examiner

*Primary Examiner* — Anner Holder
(74) *Attorney, Agent, or Firm* — Pearl Cohen Zedek Latzer Baratz LLP

(57) ABSTRACT

A system and method may allow editing of an image stream, which may be produced by, for example, an ingestible capsule. A workstation accepts images acquired by the capsule and displays the images on a monitor as a moving image. The editing method may include, for example, selecting images which follow predetermined criteria. A shortened movie may thus be created.

19 Claims, 3 Drawing Sheets

SYSTEM AND METHOD FOR EDITING AN IMAGE STREAM CAPTURED IN VIVO

PRIOR APPLICATION DATA

The present application is a continuation of prior U.S. application Ser. No. 10/949,220, filed on Sep. 27, 2004, now U.S. Pat. No. 7,986,337 entitled "SYSTEM AND METHOD FOR EDITING AN IMAGE STREAM CAPTURED IN VIVO", incorporated by reference herein in its entirety.

FIELD OF THE INVENTION

The present invention relates to a method and system for editing an image stream captured in-vivo. More specifically, the present invention relates to systems and methods for editing an image stream captured in vivo according to a pre-defined criteria.

BACKGROUND OF THE INVENTION

When viewing a movie, for example a moving image stream which may be used for medical diagnosis, a viewer may desire to view certain portions or frames, or may wish to view a short preview only, summarizing specific frames only and skipping others, for example, according to a pre-set criteria.

For example, an in vivo imager system which is carried by an ingestible capsule may be used to image lumens within a patient. The imager system captures and transmits, for example, images of the GI tract to an external recording device while the capsule passes through the GI lumen. Such an in vivo imaging system provides a platform from which moving or still images of a lumen may be viewed. Large numbers of images may be collected for viewing. For example, the images may be combined in sequence, and a moving image of, for example, more then 120 minutes in length, may be presented to the user. It would be desirable to enable a user, for example a physician, to view a short summary of the entire capture length, thus saving the viewing physician critical time, while still enabling a reliable, correct diagnosis based on the generated summary.

SUMMARY OF THE INVENTION

An exemplary embodiment of the present invention provides a system and method for editing an image stream, the image stream preferably being produced by an in vivo imaging device such as an ingestible capsule. A workstation accepts images and displays the images on a monitor such as, for example, a moving image. A user may select an editing method to create an edited film, and watch the edited films created.

The stream editing methods can include any number of methods based on pre-determined frame selection and frame skipping, or methods based on recognition of pre-determined image pertaining to a known symptom, such as bleeding and/or ulcers, etc.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1:
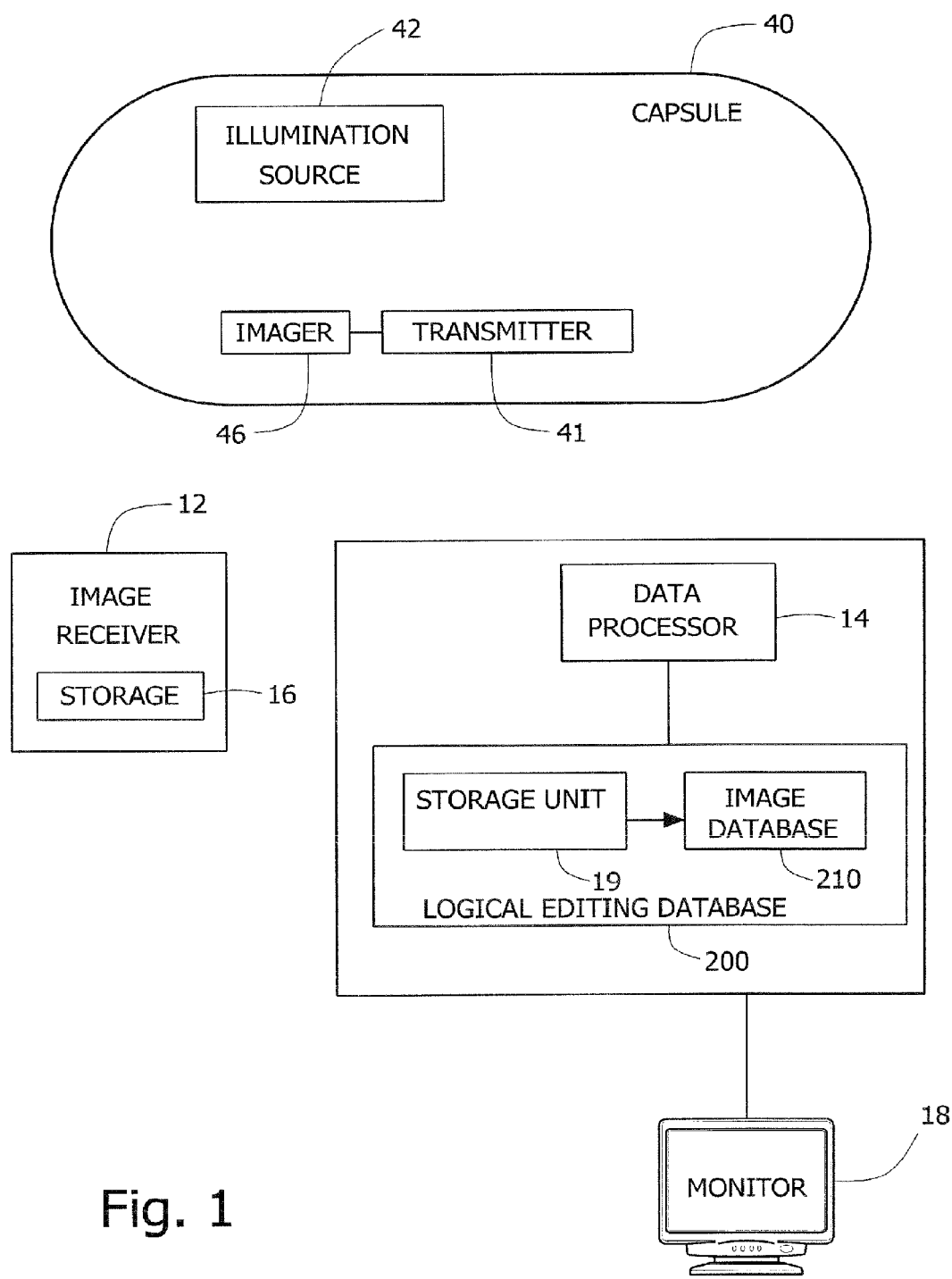
FIG. 1 shows a schematic diagram of an in vivo imaging system according to one embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. It will be appreciated that a variety of programming languages may be used to implement the teachings of the invention as described herein.

Some embodiments of the present invention are directed to a typically swallowable in-vivo device, such as an autonomous swallowable capsule. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in International Application WO 01/65995 and/or in U.S. Pat. No. 5,604,531, each of which are assigned to the common assignee of the present invention and each of which are hereby incorporated by reference. Of course, devices and systems as described herein may have other configurations and other sets of components.

Reference is made to FIG. 1, which shows a schematic diagram of an in vivo imaging system according to one embodiment of the present invention.

According to some embodiments, the system may include a device, for example a capsule 40. Capsule 40 may be implemented using a swallowable capsule, but other sorts of devices or suitable implementations may be used. According to one embodiment, capsule 40 may communicate with an external receiving and display system to provide display of data, control, or other functions. For example, power may be provided by an internal battery or a wireless receiving system. Other embodiments may have other configurations and capabilities.

In an exemplary embodiment, the system comprises a capsule 40 having an imager 46, for capturing images, an illumination source 42, for illuminating the body lumen, and a transmitter 41, for transmitting image and possibly other information to a receiving device. An optical system, including, for example, lenses or mirrors, may aid in focusing reflected light onto the imager 46.

Preferably, located outside the patient's body in one or more locations, are an image receiver 12, preferably including an antenna or antenna array, an image receiver storage unit 16, a data processor 14, a data processor storage unit 19, and an image monitor 18, for displaying, inter alia, the images recorded by the capsule 40. Preferably, the image receiver 12 and image receiver storage unit 16 are small and portable, and are worn on the patient's body during recording of the images. According to embodiments of the present invention, data processor storage unit 19 includes an image database 210 and a logical editing database 200. According to one embodiment logical editing database 200 includes predefined criteria with rules relating to which selected images, stored in the image database, should be displayed to the viewer, for example a selection of rules for displaying one out of any hundred frames captured, or rules for scanning and selecting pre-determined images pertaining to a known symptom, such as or bleeding or ulcers.

According to one embodiment of the present invention, data processor 14, data processor storage unit 19 and monitor 18 are part of a personal computer or workstation which includes standard components such as processor 14, a memory, a disk drive, and input-output devices, although alternate configurations are possible, and the system and method of the present invention may be implemented on various suitable computing systems.

Data processor 14 may include any standard data processor, such as a microprocessor, multiprocessor, accelerator board, or any other serial or parallel high performance data processor. Image monitor 18 may be a computer screen, a conventional video display, or any other device capable of providing image or other data.

Preferably, the imager 46 is a suitable CMOS camera, such as a "camera on a chip" type CMOS imager specified by Given Imaging Ltd. of Israel and designed by Photobit Corporation of California, USA. In alternate embodiments, the imager 46 may be another device, for example, a CCD. The illumination source 42 may be, for example, one or more light emitting diodes, or another suitable light source.

In operation, imager 46 captures images and sends data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to the data processor 14 or the data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data is then transferred from the image receiver storage unit 16 to the image database 210 within data processor storage unit 19. Data processor 14 may analyze and edit the data, inter alia according to the logical editing database 200, and provide the analyzed and edited data to the image monitor 18, where a health professional views the image data. Data processor 14 operates software which, in conjunction with basic operating software such as an operating system and device drivers, controls the operation of data processor 14. According to one embodiment, the software controlling data processor 14 includes code written in the C++ language and possibly additional languages, but may be implemented in a variety of known methods.

The image data collected and stored may be stored indefinitely, transferred to other locations, or manipulated or analyzed. A health professional may use the images to diagnose pathological conditions of for example the GI tract (e.g., the esophagus), and, in addition, the system may provide information about the location of these pathologies. While using a system where the data processor storage unit 19 first collects data and then transfers data to the data processor 14, the image data is not viewed in real time, other configurations allow for real time viewing.

For example, according to one embodiment, while watching the stream of generated data from an in vivo device, the viewer can employ an editing method from logical editing database 200 and view only a selection of images according to the predefined criteria of the logical database 200.

The image monitor 18 presents the image data, preferably in the form of still and moving pictures, and in addition may present other information. In an exemplary embodiment, such additional information may include, but is not limited to, absolute time elapsed for the current image being shown and summary information. Absolute time elapsed for the current image being shown may be, for example, the amount of time that elapsed between the moment the capsule 40 was first activated and the image receiver 12 started receiving transmission from the capsule 40 and the moment that the current image being displayed was captured. In other embodiments, time elapsed may be other measures, such as time elapsed from the start of a moving image to the current point. In further embodiments measures such as number of frames elapsed may be used. In an exemplary embodiment, the various categories of information may be displayed in windows. Multiple monitors may be used to display image and other data.

According to one embodiment, the in vivo imager system collects a series of still images as it traverses the GI tract. The images may be later presented as, for example, a stream of images or a moving image of the traverse of the GI tract. The in vivo imager system may collect a large volume of data, as the capsule 40 may take several hours to traverse the GI tract, and may record images at a rate of, for example, two images every second, resulting in the recordation of thousands of images. The image recordation rate (or frame capture rate) may be varied.

Preferably, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (i.e., 0-255) brightness value. According to one embodiment, images are stored sequentially in data processor storage unit 19. The stored data may be comprised of one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle etc.

Preferably, data processor storage unit 19 stores a series of images recorded by a capsule 40. The images the capsule 40 records as it moves through a patient's GI tract may be combined consecutively to form a moving image. This moving image may be displayed in a window on monitor 18. The moving image may be frozen to view one frame, speeded up, or reversed. According to one embodiment sections may be skipped automatically or by a user according to a predefined criteria, stored in the logic database 200. While the following discussion relates to the case where data from a capsule 40 is stored for later use, the system and method of the present invention may be used with systems allowing for real time viewing of image data.

In an exemplary embodiment, the moving image is stored as a series of images in the image database 210, and logic editing methods or rules are stored in the logic database 200. Image database 210 and logic database 200 may be implemented in a variety of known manners. While, in an exemplary embodiment, image database 210 and logic database 200 are stored in the same general storage unit, in alternate embodiments image database 210 and logic database 200 may be stored separately. Furthermore, the information stored in image database 210 and logic database 200 may be stored in various combinations; for example, image and logic editing rules/methods may be stored in the same database. Preferably, the entry in the logic database 200 corresponding to the edited image in the image database 210 includes a link, such as a pointer or a database reference, to the image in the image database 210 or to a database record corresponding to the image. The link may include, for example, the relative time the image was captured or an image frame number. In alternate embodiments sets or series of images may be stored in an annotation. In further embodiments, no such links are needed, as the image data and editing data may be stored in the same database. In alternate embodiments other series of steps may be used to carry out the present invention.

When used herein, "predefined criteria" and its derivatives may indicate any kind of logical method/rules for example rules that select frames according to a parameter. The parameter may be numerically based, as in selecting one image in every hundred or two hundred images generated for viewing. According to some embodiments the parameter may be image quality based, for example selecting the most qualitative image from each group of images. Other methods of editing may be based on different criteria such as logic scanning for a certain pre-defined area or image in the image database 210, such as medical diagnosis automatic scan for internal bleeding based on color differentiation within the image or percentage of resemblance to a pre-existing image in the database, which may be similar to that described in U.S. patent application Ser. No. 10/097,096 titled "METHOD AND SYSTEM FOR DETECTING COLORIMETRIC ABNORMALITIES IN VIVO", to the same assignee, which is incorporated by reference in its entirety.

According to some embodiments of the present invention, the user can also define and create an editing method according to specific needs, and choose how many or which specific frames to display. A specific time frame can be set for each body area, for example viewing every third image generated from the esophagus and every $30^{th}$ image generated from the stomach lumen. Additionally, according to some embodiments, a number of editing methods may be combined and employed, for example scanning for suspected bleeding areas and displaying every third frame of the scan's results.

When viewing the moving image, according to one embodiment, the user is presented with three windows on monitor 18. An image window provides the moving image, or still portions of that image. Such a window may include buttons or other controls which may alter the display of the image; for example, stop, play, pause, capture image, step, fast-forward, rewind, or other controls. Such controls may be activated by, for example, a pointing device such as a mouse or trackball.

According to one embodiment of the present invention, the user may switch from one editing system to the other while data is being streamed. A message window announcing/confirming the switch may be prompted, and the area and time frame of the resulting images may be displayed together with all relevant details pertaining to the selected editing system.

According to some embodiments, a timeline window may provide a timeline, an indication of the total time elapsed for the moving image, and may provide other information based on the selected editing method, such as the total time of the moving image and the percentage of frames displayed out of the entire capture device output, and what the viewer summaries based on the selected editing method.

In an exemplary embodiment, the timeline may be a bar labeled with time units, having different color visually attached to the timeline at portions which indicate the time elapsed for the portions associated with the annotations.

Figure 2:
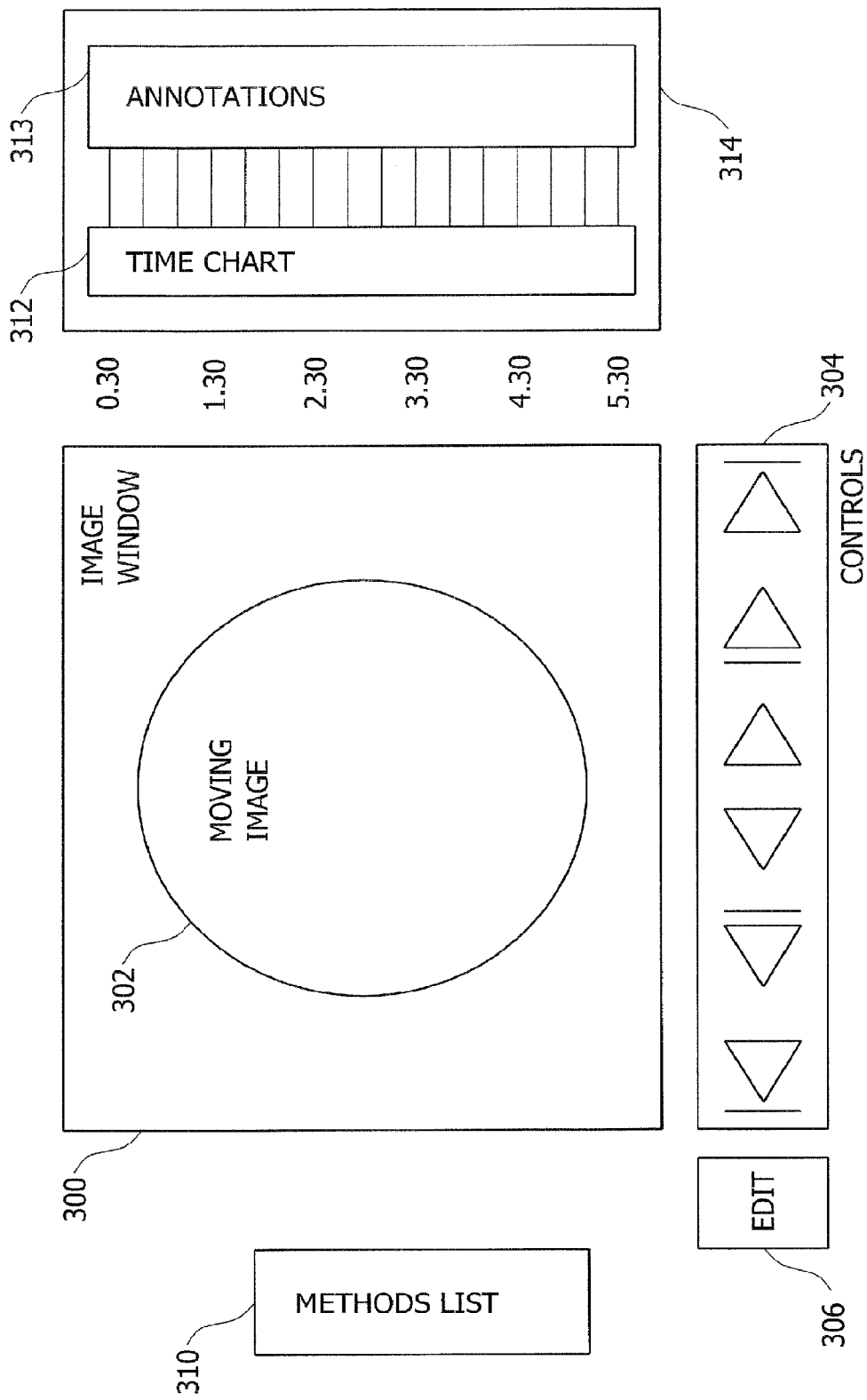
FIG. 2 is a representation of an image and a set of steering and editing tools displayed on the monitor of FIG. 1, according to one embodiment of the present invention.

FIG. 2 depicts a representation of an image and a control area displayed on the monitor 18 of FIG. 1, according to one embodiment of the present invention. The image window 300 displays the moving image 302, or still portions of the moving image 302. Controls 304 may alter the display of the moving image 302. An edit control 306 allows a user to select an editing method, for example, from a list of available methods listed in chart 310.

According to some embodiments of the present invention, a different controls 304 button is assigned to each editing method. For example, for a method based on a suspected blood indicator (SBI) scan, a navigation window may pop up with buttons enabling image freeze, fast forward and rewind options etc. Timeline window 314 provides a timeline or time chart 312, and includes summaries 313 of annotations, with reference to the appropriate relative time on the time chart 312 based on the selected editing method.

Figure 3:
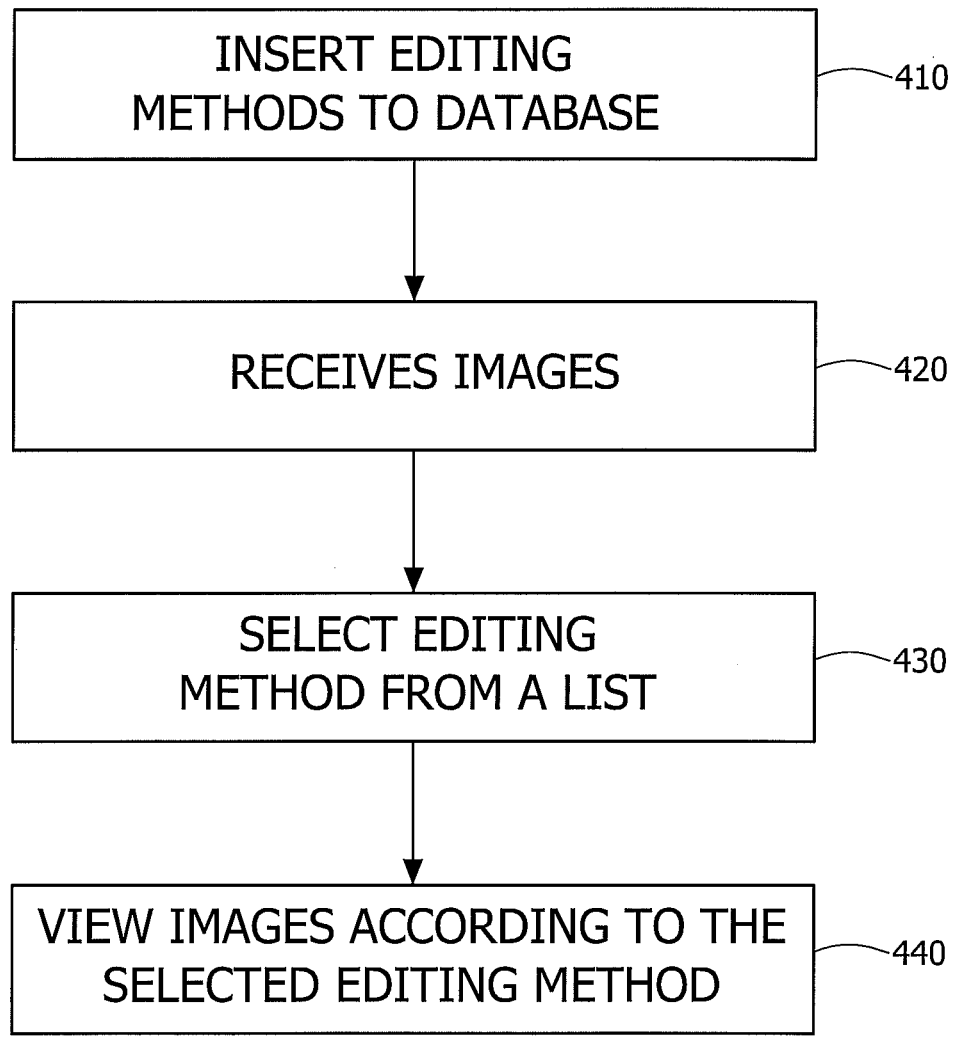
FIG. 3 depicts a flowchart for viewing an edited moving image according to a selected logical editing method, according to one embodiment of the present invention.

FIG. 3 depicts a flowchart for viewing a moving image based on a selected editing method, according to one embodiment of the present invention. In step 410 different editing methods are introduced to the in vivo imaging system. The editing methods may be stored in the logical editing database 200, for example as an editing method list. According to some embodiments the user may select the editing method before the output movie is stored in the image database, after such a movie has been stored or during playback of the stored movie.

In step 420 the system receives a list of image frames and may store them in the image database. In step 430, the user may select an editing method from the editing method list. Preferably, the user presses a control, such as the select editing method image button 306 to select the desired editing method. In step 440 the user may view the image streams which resulted from the editing method he selected. According to some embodiments of the present invention, each method is assigned a specific tool window, enabling easy and effective use of the editing system.

For example, for an editing method which displays a summary movie compiled from every tenth frame, specific buttons are assigned, enabling movie playback, frame freeze, fast forward and rewind options.

In addition, according to some embodiments, an editing system select button is available, enabling the user to switch frame selection and editing methods in cases where a more detailed view is necessary. This button will enable the user to easily toggle between editing methods and switch, for example, from a summary view of every $20^{th}$ frame to a more detailed movie summarizing every second frame. The user can thus employ different methods for every time frame recorded, or every body area imaged. The user may also toggle a switch between methods based on numerical selection of frames to SBI mode or edit findings mode.

According to some embodiments the user may enter annotation information, such as a textual description of the image using, for example, a keyboard. The annotation may be stored in an entry in an annotation database. Preferably, an entry in the annotation database corresponding to an annotated image in the image database 210 includes a link, such as a pointer or a database reference, to the image in the image database or to a database record corresponding to the image. The link may include, for example, the relative time the image was captured or an image frame number. In alternate embodiments sets or series of images may be stored in an annotation.

A user may view and edit an annotation. Typically, a user first selects the annotation by, for example, using a pointing device to indicate the annotation in the timeline window or the annotation window. Annotations or annotation summaries may appear in areas other than a timeline or annotation window. The full text or representation of the annotation appears or is otherwise displayed or output, and the user may, for example, read or edit the text, for example in a pop-up window. The user may see an enlarged view of the image or set of images included in the annotation. If the annotation includes a set of images, the user may view the set of images as a moving image. According to some embodiments an image stream, based on the annotation may be created. Preferably, an entry in the annotation database corresponding to an annotated image in the image database 210 includes a link, such as a pointer or a database reference, to the image in the image database or/and to the logical editing database 200 record corresponding to the image.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for editing an image stream captured in vivo, the method comprising:
   capturing a set of images by an in-vivo device disposed within a body lumen;
   transferring the set of captured images to a workstation;
   selecting, by user action, a first editing method, said first editing method automatically selecting a first subset of the captured images that satisfy the first editing method and displaying the first subset of the captured images as a first summary movie; and
   selecting, by user action, a second editing method different from the first editing method, said second editing method automatically selecting a second subset of the captured images that satisfy the second editing method, and automatically switching to displaying a second summary movie comprising the second subset of the captured images, wherein the first subset of the captured images is different than the second subset of the captured images.

2. The method of claim 1, wherein each of the first and second subsets of the captured images include one image from every group of a different predetermined number of consecutive images of the captured images.

3. The method of claim 1, wherein the first and second editing methods are different editing methods selected from the group consisting of: selecting images based on a color differentiation criteria, selecting images based on an annotation based criteria, selecting images based on the image quality, and selecting one image from every group of a predetermined number of consecutive images of the captured images.

4. The method of claim 1, wherein the second editing method includes a combination of the first editing method and an additional editing method.

5. The method of claim 1 comprising switching between the first and second editing methods for viewing different body areas.

6. The method of claim 1 comprising switching to displaying the second summary movie while the first summary movie is being displayed.

7. The method of claim 1, wherein one or both of the first and second editing methods is selected by a user from a list of available editing methods.

8. The method of claim 1, wherein each of the first and second subsets include an image not in the other subset.

9. The method of claim 1 comprising displaying the first and second summary movies on a monitor.

10. The method of claim 1, wherein the images are captured in a gastrointestinal tract by an in-vivo capsule device.

11. A system for editing an image stream captured in vivo, the system comprising:
    a memory to store a set of captured images by an in-vivo device disposed within a body lumen;
    a processor configured to:
    select, by user action, a first editing method, and use said first editing method to automatically select a first subset of the captured images that satisfy the first editing method, and to provide the first subset to an image monitor for displaying the first subset as a first summary movie; and select, by user action, a second editing method different from the first editing method, and use said second editing method to automatically select a second subset of the captured images that satisfy the second editing method, and automatically cause the image monitor to switch to displaying a second summary movie comprising the second subset of the captured images, wherein the first subset of the captured images is different than the second subset of the captured images.

12. The system of claim 11, wherein each of the first and second subsets of the captured images include one image from every group of a different predetermined number of consecutive images of the captured images.

13. The system of claim 11, wherein the first and second editing methods are different editing methods selected from the group consisting of: selecting images based on a color differentiation criteria, selecting images based on an annotation based criteria, selecting images based on the image quality, and selecting one image from every group of a predetermined number of consecutive images of the captured images.

14. The system of claim 11, wherein the second editing method includes a combination of the first editing method and an additional editing method.

15. The system of claim 11 wherein the processor is configured to cause the image monitor to switch between the first and second editing methods for viewing different body areas.

16. The system of claim 11 wherein the processor is configured to cause the image monitor to switch to displaying the second summary movie while the first summary movie is being displayed.

17. The system of claim 11, wherein one or both of the first and second editing methods is selected by a user from a list of available editing methods.

18. The system claim 11, wherein each of the first and second subsets include an image not in the other subset.

19. The system of claim 11, wherein the images are captured in a gastrointestinal tract by an in-vivo capsule device.

* * * * *